(12) United States Patent
Luo et al.

(10) Patent No.: US 10,161,873 B2
(45) Date of Patent: Dec. 25, 2018

(54) FLUORESCENT MICROSCOPIC IMAGING METHOD AND APPARATUS

(71) Applicant: SHANGHAI RUIYU BIOTECH CO., LTD., Shanghai (CN)

(72) Inventors: Puwen Luo, Shanghai (CN); Haohan Xia, Shanghai (CN)

(73) Assignee: SHANGHAI RUIYU BIOTECH CO., LTD., Shanghai (CN)

( * ) Notice: Subject to any disclaimer, the term of this patent is extended or adjusted under 35 U.S.C. 154(b) by 0 days.

(21) Appl. No.: 15/738,296

(22) PCT Filed: May 20, 2016

(86) PCT No.: PCT/CN2016/082768
§ 371 (c)(1),
(2) Date: Dec. 20, 2017

(87) PCT Pub. No.: WO2017/000701
PCT Pub. Date: Jan. 5, 2017

(65) Prior Publication Data
US 2018/0188178 A1  Jul. 5, 2018

(30) Foreign Application Priority Data

Jul. 1, 2015 (CN) .......................... 2015 1 0376530
Jul. 28, 2015 (CN) .......................... 2015 1 0452593

(51) Int. Cl.
*G01N 21/01* (2006.01)
*G01N 21/64* (2006.01)

(52) U.S. Cl.
CPC ......... *G01N 21/6458* (2013.01); *G01N 21/01* (2013.01); *G01N 21/64* (2013.01);
(Continued)

(58) Field of Classification Search
CPC ............... G01N 21/6456; G01N 21/64; G01N 21/6458; G01N 2201/062;
(Continued)

(56) References Cited

U.S. PATENT DOCUMENTS

| 5,187,572 A | 2/1993 | Nakamura et al. |
| 8,785,885 B1 | 7/2014 | Jutamulia et al. |

(Continued)

FOREIGN PATENT DOCUMENTS

| CN | 202057599 U | 11/2011 |
| CN | 102305778 A | 1/2012 |

(Continued)

OTHER PUBLICATIONS

International Search Report and Written Opinion for International Application No. PCT/CN2016/082768, dated Aug. 23, 2016—17 Pages.

(Continued)

*Primary Examiner* — David P Porta
*Assistant Examiner* — Faye Boosalis
(74) *Attorney, Agent, or Firm* — RatnerPrestia

(57) ABSTRACT

A fluorescence microscopic imaging method includes: after a to-be-detected sample plate is placed, lightening, according to experimental requirements, at least one monochromatic fluorescence excitation light source with a same color among multiple monochromatic fluorescence excitation light sources as a target light source, where monochromatic fluorescence excitation light emitted by each monochromatic fluorescence excitation light source obliquely enters a preset detection region of the to-be-detected sample plate; collecting, at a side of the to-be-detected sample plate facing away from the target light source, fluorescence of particles within the preset detection region excited by irradiation of monochromatic fluorescence excitation light emitted by the (Continued)

target light source, and magnifying the preset detection region a preset number of times; filtering the excited fluorescence of the particles within the preset detection region; and acquiring a fluorescence image of the preset detection region.

11 Claims, 4 Drawing Sheets

(52) U.S. Cl.
CPC ............... *G01N 2021/6471* (2013.01); *G01N 2021/6478* (2013.01); *G01N 2201/061* (2013.01); *G01N 2201/062* (2013.01)

(58) Field of Classification Search
CPC ......... G01N 2021/6478; G01N 21/645; G01N 2201/061; G01N 2021/6471; G01N 21/01
See application file for complete search history.

(56) References Cited

U.S. PATENT DOCUMENTS

| | | | |
|---|---|---|---|
| 2005/0057798 A1 | 3/2005 | Osborne et al. | |
| 2009/0152474 A1 | 6/2009 | Berger et al. | |
| 2011/0168918 A1 | 7/2011 | Wimberger-Friedl et al. | |
| 2011/0312105 A1 | 12/2011 | Tan et al. | |
| 2012/0016230 A1* | 1/2012 | Kishima | A61B 1/00186 600/425 |
| 2013/0099120 A1 | 4/2013 | Chan et al. | |
| 2013/0105371 A1 | 5/2013 | Frorip et al. | |
| 2013/0201322 A1 | 8/2013 | Park et al. | |
| 2015/0008337 A1 | 1/2015 | Shimizu | |

FOREIGN PATENT DOCUMENTS

| | | |
|---|---|---|
| CN | 102341696 A | 2/2012 |
| CN | 102370462 A | 3/2012 |
| CN | 102834718 A | 12/2012 |
| CN | 102946918 A | 2/2013 |
| CN | 103134780 A | 6/2013 |
| CN | 203337549 U | 12/2013 |
| CN | 102165305 B | 8/2014 |
| CN | 104204778 A | 12/2014 |
| CN | 204330595 U | 5/2015 |
| CN | 104990907 A | 10/2015 |
| CN | 105092550 A | 11/2015 |
| CN | 105158220 A | 12/2015 |
| CN | 205091263 U | 3/2016 |
| CN | 104568859 B | 10/2017 |
| JP | 2005062023 A | 3/2005 |
| JP | 2004325174 A | 11/2014 |
| WO | 2014191003 A1 | 12/2014 |

OTHER PUBLICATIONS

European Search Report issued in EP 16 817 065.2 dated Oct. 29, 2018, 8 pages.

* cited by examiner

FLUORESCENT MICROSCOPIC IMAGING METHOD AND APPARATUS

The present application is a National Stage application of PCT international patent application PCT/CN2016/082768, filed on May 20, 2016 which claims priority to Chinese Patent Application No. 201510376530.0, titled "INTEGRATED FLUORESCENCE EXCITATION LIGHT SOURCE APPARATUS", filed on Jul. 1, 2015 with the State Intellectual Property Office of People's Republic of China, and priority to Chinese Patent Application No. 201510452593.X, titled "FLUORESCENT MICROSCOPIC IMAGING METHOD AND APPARATUS", filed on Jul. 28, 2015 with the State Intellectual Property Office of People's Republic of China, all of which are incorporated herein by reference in their entireties.

FIELD

The present disclosure relates to the technical field of fluorescence microscopic imaging, and in particular to a fluorescence microscopic imaging method and a fluorescence microscopic imaging apparatus.

BACKGROUND

Reference is made to FIG. 1, which shows a fluorescence microscopic imaging apparatus according to the conventional technology. The fluorescence microscopic imaging apparatus includes: a fluorescence excitation light source 1, a dichroic mirror 2 arranged to form an angle of 45 degrees with an irradiation direction of the monochromatic fluorescence excitation light source 1, an objective lens 3, a sample placing platform 4, an emitting light filter 5 and a camera 6. The monochromatic fluorescence excitation light source 1 emits excitation light, and the excitation light is reflected to the objective lens 3 through the dichroic mirror 2, and then irradiates to a to-be-detected sample plate on the sample placing platform 4. Particles within the to-be-detected sample plate emit fluorescence due to excitation, and the fluorescence enters the camera 6 to generate an image after passing through the dichroic mirror 2 and the emitting light filter 5. The conventional fluorescence microscopic imaging apparatus needs to separate light using the dichroic mirror, and thereby resulting in that the fluorescence microscopic imaging apparatus has a complicated structure and a high cost.

SUMMARY

In view of above, a fluorescence microscopic imaging method and a fluorescence microscopic imaging apparatus are provided according to an aspect of the present disclosure. No dichroic mirror needs to be provided to separate light, such that the fluorescence microscopic imaging apparatus has a simple structure and a low cost; and monochromatic fluorescence excitation light entering an objective lens is reduced, and thereby acquiring a more accurate fluorescence image.

In order to achieve the above, technical solutions provided by the present disclosure are as follows.

A fluorescence microscopic imaging method is provided, which includes: after a to-be-detected sample plate is placed, lightening, according to an experimental requirement, at least one monochromatic fluorescence excitation light source with a same color among multiple monochromatic fluorescence excitation light sources as a target light source, where monochromatic fluorescence excitation light emitted by each of the multiple monochromatic fluorescence excitation light sources obliquely enters a preset detection region of the to-be-detected sample plate;

collecting, at a side of the to-be-detected sample plate facing away from the target light source, fluorescence of particles within the preset detection region excited by irradiation of monochromatic fluorescence excitation light emitted by the target light source, and magnifying the preset detection region a preset number of times;

filtering the excited fluorescence of the particles within the preset detection region; and acquiring a fluorescence image of the preset detection region.

Preferably, after the target light source is lightened and before the monochromatic fluorescence excitation light emitted by the target light source enters the to-be-detected sample plate, the method further includes: converging the monochromatic fluorescence excitation light emitted by each monochromatic fluorescence excitation light source among the target light source.

A fluorescence microscopic imaging apparatus is further provided according to the present disclosure, which includes: a light source device, a sample placing platform, an objective lens, an emitting light filtering module and an image acquisition device. The light source device includes multiple monochromatic fluorescence excitation light sources and a control system electrically connected to the multiple monochromatic fluorescence excitation light sources. The multiple monochromatic fluorescence excitation light sources are arranged around a central axis of an imaging light path composed of the objective lens and the image acquisition device, and monochromatic fluorescence excitation light emitted by each of the multiple monochromatic fluorescence excitation light sources and the central axis of the imaging light path intersect at a preset position on the sample placing platform. The control system lightens, according to an experimental requirement, at least one monochromatic fluorescence excitation light source with a same color among the multiple monochromatic fluorescence excitation light sources as a target light source. The sample placing platform is arranged at a position where monochromatic fluorescence excitation light emitted by the multiple monochromatic fluorescence excitation light sources intersects and is configured to place a to-be-detected sample plate, a preset detection region of the to-be-detected sample plate is arranged at the preset position on the sample placing platform. The objective lens is arranged at a side of the sample placing platform facing away from the light source device. The emitting light filtering module is arranged at a side of the objective lens facing away from the sample placing platform. The image acquisition device is arranged at a side of the emitting light filtering module facing away from the objective lens.

Preferably, the light source device further includes a bright field light source, full-band white light emitted by the bright field light source is toward the sample placing platform and coincides with the central axis of the imaging light path.

Preferably, the monochromatic fluorescence excitation light source is a monochromatic LED fluorescence excitation light source.

Preferably, the light source device further includes an excitation light filter arranged in an irradiation direction of the monochromatic LED fluorescence excitation light source and arranged between the monochromatic LED fluorescence excitation light source and the sample placing platform.

Preferably, the monochromatic fluorescence excitation light source includes:

a white light excitation light source; and an excitation light filter arranged in an irradiation direction of the white light excitation light source and arranged between the white light excitation light source and the sample placing platform.

Preferably, the emitting light filtering module is an emitting light filtering turntable, multiple emitting light filtering regions are provided at a periphery of the emitting light filtering turntable, and a pass band of each of the multiple emitting light filtering regions is a band of fluorescence emitted by particles within the to-be-detected sample plate and excited by the monochromatic fluorescence excitation light source with a certain color.

Preferably, the light source device further includes a light converging module arranged in an irradiation direction of the monochromatic fluorescence excitation light source and arranged between the monochromatic fluorescence excitation light source and the sample placing platform.

Preferably, the light converging module is a light converging lens set including multiple lenses or a light converging lens.

Preferably, the image acquisition device is an eyepiece or a camera.

As compared with the conventional technology, the technical solutions provided by the present disclosure have at least the following advantages.

A fluorescence microscopic imaging method and a fluorescence microscopic imaging apparatus are provided according to the present disclosure. The method includes: lightening, according to an experimental requirement, at least one monochromatic fluorescence excitation light source with a same color among multiple monochromatic fluorescence excitation light sources as a target light source, where monochromatic fluorescence excitation light emitted by each of the multiple monochromatic fluorescence excitation light sources obliquely enters a preset detection region of the to-be-detected sample plate; collecting, at a side of the to-be-detected sample plate facing away from the target light source, fluorescence of particles within the preset detection region excited by irradiation of monochromatic fluorescence excitation light emitted by the target light source, and magnifying the preset detection region a preset number of times; filtering the excited fluorescence of the particles within the preset detection region; and acquiring a fluorescence image of the preset detection region.

According to the above content, with the technical solutions provided by the present disclosure, no dichroic mirror needs to be provided to separate monochromatic fluorescence excitation light from fluorescence, such that the fluorescence microscopic apparatus has a simple structure and a low cost, and it is avoided light energy loss due to fluorescence passing through the dichroic mirror, and thereby acquiring a more bright and clear fluorescence image. In addition, the monochromatic fluorescence excitation light source obliquely irradiates the to-be-detected sample plate, such that a small amount of monochromatic fluorescence excitation light enters the objective lens after passing through the to-be-detected sample plate, and thereby reducing influence from the monochromatic fluorescence excitation light during later imaging and acquiring a more accurate fluorescence image.

BRIEF DESCRIPTION OF THE DRAWINGS

In order to illustrate technical solutions in embodiments of the present disclosure or the conventional technology more clearly, hereinafter drawings to be used in the description of the embodiments or the conventional technology are introduced simply. Apparently, the drawings described below only describe the embodiments of the present disclosure, and other drawings may be obtained based on the provided drawings by those skilled in the art without any creative work.

DETAILED DESCRIPTION OF THE EMBODIMENTS

Hereinafter technical solutions in embodiments of the present disclosure are described clearly and completely in conjunction with drawings in the embodiments of the present disclosure. Apparently, the described embodiments are only some rather than all of the embodiments of the present disclosure. Any other embodiments obtained based on the embodiments of the present disclosure by those skilled in the art without any creative work fall within the scope of protection of the present disclosure.

As described in the background, since the conventional fluorescence microscopic imaging apparatus needs to separate light using a dichroic mirror, resulting in that the fluorescence microscopic imaging apparatus has a complicated structure and a high cost.

Based on the above content, a fluorescence microscopic imaging method and a fluorescence microscopic imaging apparatus are provided according to embodiments of the present disclosure, it does not need to separate light using a dichroic mirror, such that the apparatus has a simple structure and a low cost. In addition, monochromatic fluorescence excitation light entering an objective lens is reduced, and thereby acquiring a more accurate fluorescence image.

Figure 1:
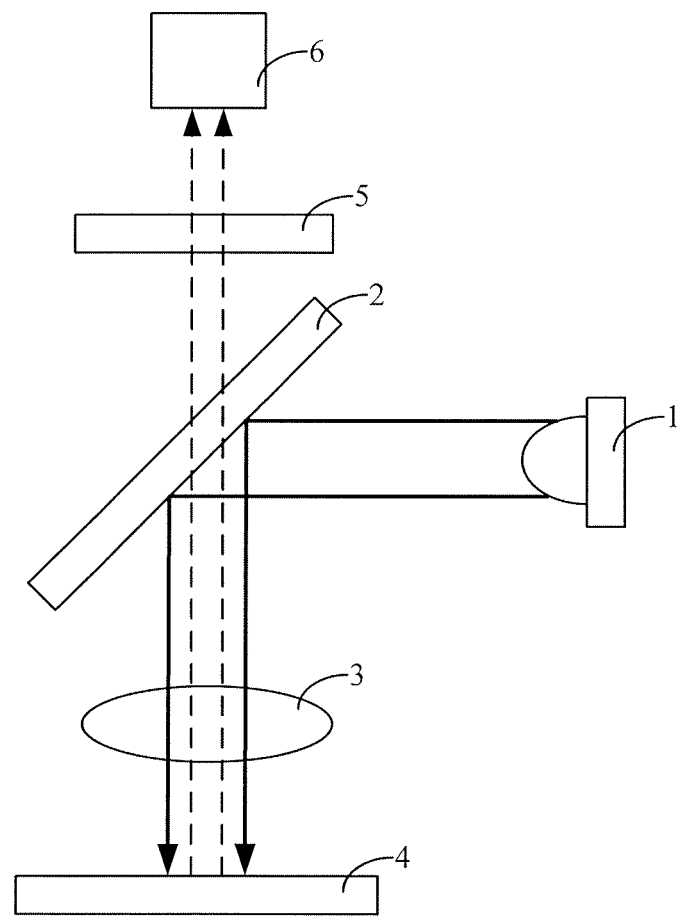
FIG. 1 is a schematic structural diagram of a fluorescence microscopic imaging apparatus according to the conventional technology.
Figure 2:
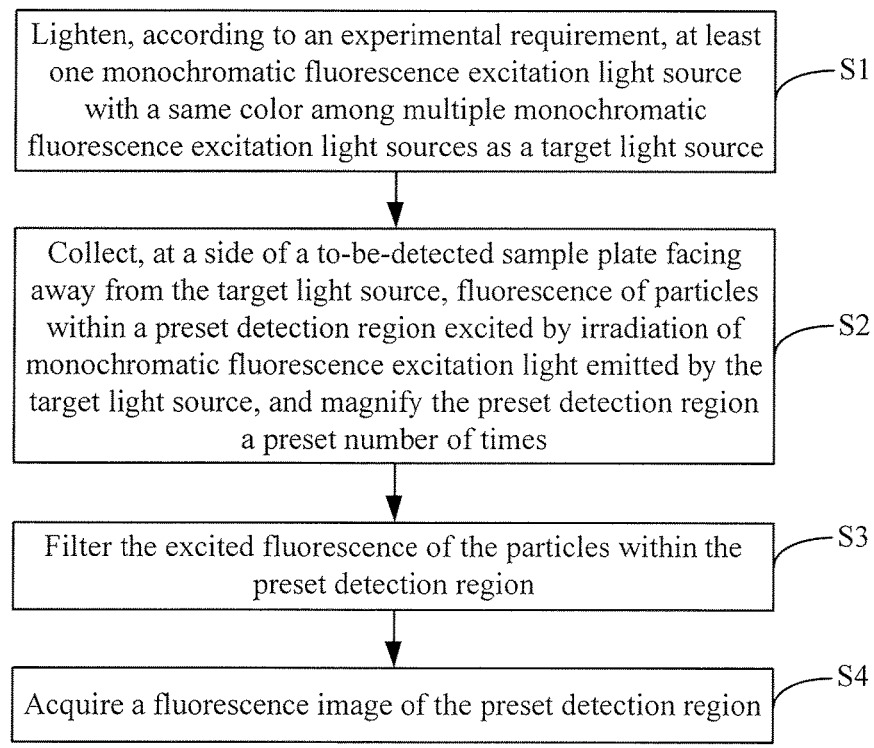
FIG. 2 is a flowchart of a fluorescence microscopic imaging method according to an embodiment of the present disclosure.

Specifically, reference is made to FIG. 2, which is a flowchart of a fluorescence microscopic imaging method according to an embodiment of the present disclosure. The method includes, after a to-be-detected sample plate is placed, step S1 to step S4 in the following.

In step S1, at least one monochromatic fluorescence excitation light source with a same color among multiple monochromatic fluorescence excitation light sources is lightened, according to an experimental requirement, as a target light source, monochromatic fluorescence excitation light emitted by each of the multiple monochromatic fluorescence excitation light sources obliquely enters a preset detection region of the to-be-detected sample plate.

In step S2, at a side of the to-be-detected sample plate facing away from the target light source, fluorescence of particles within the preset detection region excited by irradiation of monochromatic fluorescence excitation light emitted by the target light source is collected, and the preset detection region is magnified a preset number of times.

In step S3, the excited fluorescence of the particles within the preset detection region is filtered.

In step S4, a fluorescence image of the preset detection region is acquired.

The multiple monochromatic fluorescence excitation light sources provided by the embodiment of the present disclosure may include monochromatic fluorescence excitation light sources with different colors (or bands) or include monochromatic fluorescence excitation light sources with the same color (or band). The multiple monochromatic fluorescence excitation light sources being monochromatic fluorescence excitation light sources with different colors may include multiple cases as follows. That is, all the monochromatic fluorescence excitation light sources provided by the embodiment of the present disclosure have different colors. Alternatively, all the monochromatic fluorescence excitation light sources are grouped as multiple groups, monochromatic fluorescence excitation light sources in each group have the same color, and monochromatic fluorescence excitation light sources in different groups have different colors, such that multiple monochromatic fluorescence excitation light sources with the same color are lightened so as to improve brightness of fluorescence excitation light for each color, which is not limited in the present disclosure.

According to the above content, with the technical solutions provided by the embodiments of the present disclosure, no dichroic mirror needs to be provided to separate monochromatic fluorescence excitation light from fluorescence, such that the fluorescence microscopic apparatus has a simple structure and a low cost, and it is avoided light energy loss due to fluorescence passing through the dichroic mirror, and thereby acquiring a more bright and clear fluorescence image. In addition, the monochromatic fluorescence excitation light source obliquely irradiates the to-be-detected sample plate, such that a small amount of monochromatic fluorescence excitation light enters the objective lens after passing through the to-be-detected sample plate, and thereby reducing influence from the monochromatic fluorescence excitation light during later imaging and acquiring a more accurate fluorescence image.

Furthermore, in order to improve brightness of fluorescence excitation light emitted by the monochromatic fluorescence excitation light sources and thus to improve brightness of the monochromatic fluorescence excitation light emitted by the target light source, after the target light source is lightened and before the monochromatic fluorescence excitation light emitted by the target light source enters the to-be-detected sample plate, the method further includes: converging the monochromatic fluorescence excitation light emitted by each monochromatic fluorescence excitation light source among the target light source.

Figure 3:
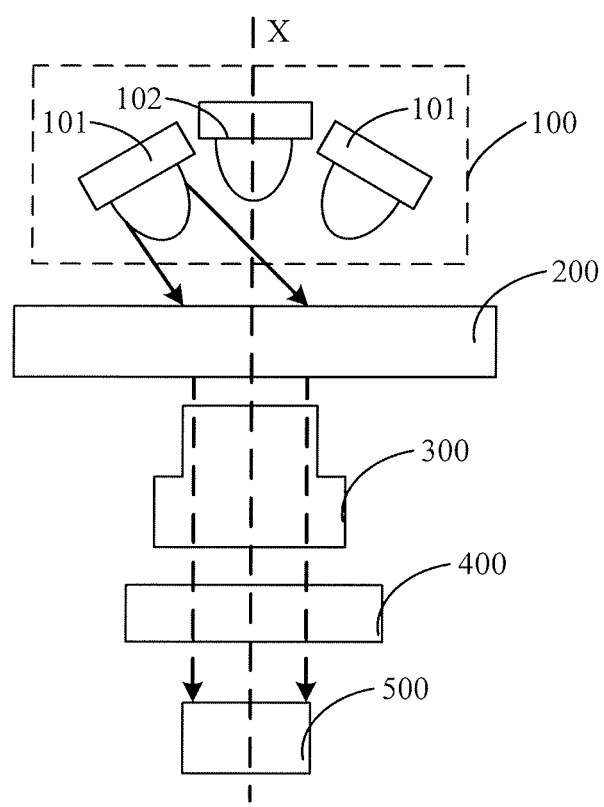
FIG. 3 is a schematic structural diagram of a fluorescence microscopic imaging apparatus according to an embodiment of the present disclosure.

Reference is made to FIG. 3, which is a schematic structural diagram of a fluorescence microscopic imaging apparatus according to an embodiment of the present disclosure. The fluorescence microscopic imaging apparatus includes: a light source device 100, a sample placing platform 200, an objective lens 300, an emitting light filtering module 400 and an image acquisition device 500.

The light source device 100 includes multiple monochromatic fluorescence excitation light sources 101 and a control system (not shown) electrically connected to the multiple monochromatic fluorescence excitation light sources 101. The multiple monochromatic fluorescence excitation light sources 101 are arranged around a central axis X of an imaging light path composed of the objective lens 300 and the image acquisition device 500. Monochromatic fluorescence excitation light emitted by each monochromatic fluorescence excitation light source 101 and the central axis X of the imaging light path intersect at a preset position on the sample placing platform 200. The control system lightens at least one monochromatic fluorescence excitation light source with a same color among the multiple monochromatic fluorescence excitation light sources 101 as a target light source, according to an experimental requirement.

The sample placing platform 200 is arranged at a position where monochromatic fluorescence excitation light emitted by the multiple monochromatic fluorescence excitation light sources 101 intersects, and is configured to place a to-be-detected sample plate. A preset detection region of the to-be-detected sample plate is arranged at the preset position on the sample placing platform 200.

The objective lens 300 is arranged at a side of the sample placing platform 200 facing away from the light source device 100, and is configured to collect fluorescence of particles within the preset detection region excited by irradiation of monochromatic fluorescence excitation light emitted by the target light source and magnify the preset detection region a preset number of times.

The emitting light filtering module 400 is arranged at a side of the objective lens 300 facing away from the sample paling platform 200, and is configured to filter the excited fluorescence of the particles within the preset detection region.

The image acquisition device 500 is arranged at a side of the emitting light filtering module 400 facing away from the objective lens 300, and is configured to acquire a fluorescence image of the preset detection region. The image acquisition device may be an eyepiece or a camera or the like, which is not limited in the present disclosure.

According to the above content, the multiple monochromatic fluorescence excitation light sources provided by the embodiments of the present disclosure are arranged around the central axis of the imaging light path composed of the objective lens and the image acquisition device, and the monochromatic fluorescence excitation light emitted by each monochromatic fluorescence excitation light source and the central axis of the imaging light path intersect at a preset position on the sample placing platform. That is, the monochromatic fluorescence excitation light emitted by the monochromatic fluorescence excitation light source obliquely enters the present position on the sample placing platform. That is, the monochromatic fluorescence excitation light emitted by the monochromatic fluorescence excitation light source obliquely enters the preset detection region of the to-be-detected sample plate, such that a small amount of the monochromatic fluorescence excitation light enters the objective lens after passing through the to-be-detected sample plate, and thereby reducing influence from the monochromatic fluorescence excitation light during later imaging, and acquiring a more accurate fluorescence image.

Furthermore, as shown in FIG. 3, in the multi-fluorescence channel synchronous microscopic imaging apparatus according to the embodiment of the disclosure, the light source device 100 further includes a bright field light source 102, full-band white light emitted by the bright field light source 102 is toward the sample placing platform 200 and coincides with the central axis X of the imaging light path.

Specifically, the monochromatic fluorescence excitation light source provided by the embodiments of the present disclosure may be a monochromatic LED (Light Emitting Diode) fluorescence excitation light source. Furthermore, in order to improve unity of the monochromatic fluorescence excitation light emitted by the monochromatic LED fluorescence excitation light source, the light source device provided by the embodiments of the present disclosure further includes an excitation light filter arranged in an irradiation direction of the monochromatic LED fluorescence excitation light source and arranged between the monochromatic LED fluorescence excitation light source and the sample placing platform. Light without a band of the monochromatic fluorescence excitation light is absorbed by the excitation light filter, and only the monochromatic fluorescence excitation light passes through the excitation light filter, and thereby improving the unity of the monochromatic fluorescence excitation light emitted from the monochromatic LED fluorescence excitation light source.

Alternatively, in the embodiments of the present disclosure, the monochromatic fluorescence excitation light source may further include: a white light excitation light source; and an excitation light filter arranged in an irradiation direction of the white light excitation light source and arranged between the white light excitation light source and the sample placing platform. The white light excitation light source emits full-band white light, light with a band which is not needed is absorbed by the excitation light filter and the monochromatic fluorescence excitation light within a preset band passes through the excitation light filter. It should be noted that, the white light excitation light source provided by the embodiments of the present disclosure may be a mercury lamp or a Xenon lamp, which is not limited in the present disclosure.

It should be noted that, the LED has advantages of short response time, low energy consumption, a low cost, a long service life and a small volume, hence in the embodiments of the present disclosure, the monochromatic fluorescence excitation light source is preferably a monochromatic LED fluorescence excitation light source. In addition, the control system provided by the embodiments of the present disclosure may be a single chip microprocessor and so on, which is not limited in the present disclosure.

The emitting light filtering module provided by the embodiments of the present disclosure filters the fluorescence of particles within the preset detection region excited by the monochromatic fluorescence excitation light. The emitting light filtering module is an emitting light filtering turntable, and multiple emitting light filtering regions are provided at a periphery of the emitting light filtering turntable. A pass band of each emitting light filtering region is a band of fluorescence emitted by particles within the to-be-detected sample plate and excited by the monochromatic fluorescence excitation light source with a certain color.

For example, in a case that the target light source is a blue fluorescence excitation light source, the target light source emits blue fluorescence excitation light. After irradiating the preset detection region of the to-be-detected sample plate, the blue fluorescence excitation light excites particles within the preset detection region to emit green fluorescence; and then emitting light composed of the green fluorescence and the blue stray light enters the emitting light filtering turntable after passing through the objective lens. In this case, an emitting light filtering region in the emitting light filtering turntable where the green fluorescence passes aligns the objective lens, such that the stray light in the emitting light is absorbed and only the green fluorescence passes through the emitting light filtering turntable.

In addition, in a case that the light source device further includes a bright field light source and since the bright field light source emits full-band white light, the emitting light filtering module further includes a transparent region. That is, in a case that the target light source is the bright field light source, the transparent region in the emitting light filtering turntable corresponds to the objective lens.

Figure 4:
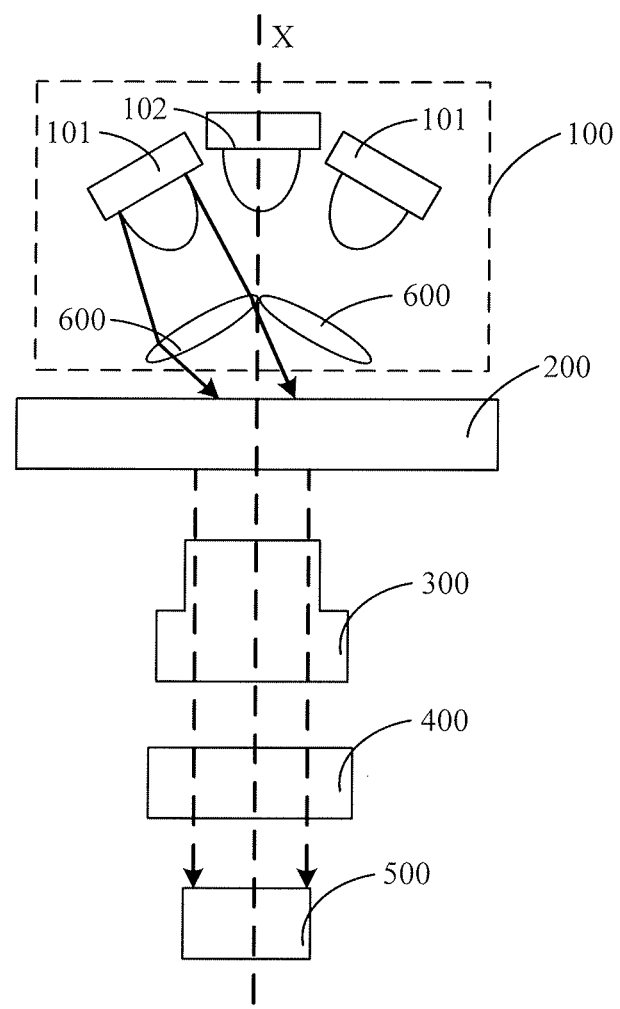
FIG. 4 is a schematic structural diagram of another fluorescence microscopic imaging apparatus according to an embodiment of the present disclosure.

Furthermore, in order to improve brightness of the monochromatic fluorescence excitation light emitted by the monochromatic fluorescence excitation light source, reference is made to FIG. 4, which is a schematic structural diagram of another fluorescence microscopic imaging apparatus according to an embodiment of the present disclosure. The light source device 100 further includes a light converging module 600 arranged in an irradiation direction of the monochromatic fluorescence excitation light source 101 and arranged between the monochromatic fluorescence excitation light source 101 and the sample placing platform 200. The light converging module may be a light converging lens set including multiple lenses or a single light converging lens, which is not limited in the present disclosure.

In order to fix the light source device, the sample placing platform, the objective lens, the emitting light filtering module and the image acquisition device and so on, all the structures may be fixed by a fixing bracket in the fluorescence microscopic imaging apparatus provided by the embodiments of the present disclosure.

A fluorescence microscopic imaging method and a fluorescence microscopic imaging apparatus are provided according to the present disclosure. The method includes: lightening, according to an experimental requirement, at least one monochromatic fluorescence excitation light source with a same color among multiple monochromatic fluorescence excitation light sources as a target light source, where monochromatic fluorescence excitation light emitted by each of the multiple monochromatic fluorescence excitation light sources obliquely enters a preset detection region of the to-be-detected sample plate; collecting, at a side of the to-be-detected sample plate facing away from the target light source, fluorescence of particles within the preset detection region excited by irradiation of monochromatic fluorescence excitation light emitted by the target light source, and magnifying the preset detection region a preset number of times; filtering the excited fluorescence of the particles within the preset detection region; and acquiring a fluorescence image of the preset detection region.

According to the above content, with the technical solutions provided by the embodiments of the present disclosure, no dichroic mirror needs to be provided to separate monochromatic fluorescence excitation light from fluorescence, such that the fluorescence microscopic apparatus has a simple structure and a low cost, and it is avoided light energy loss due to fluorescence passing through the dichroic mirror, and thereby acquiring a more bright and clear fluorescence image. In addition, the monochromatic fluorescence excitation light source obliquely irradiates the to-be-detected sample plate, such that a small amount of monochromatic fluorescence excitation light enters the objective lens after passing through the to-be-detected sample plate, and thereby reducing influence from the monochromatic fluorescence excitation light during later imaging and acquiring a more accurate fluorescence image.

The above description of the disclosed embodiments can enable those skilled in the art to implement or practice the present disclosure. Many changes to these embodiments are apparent for those skilled in the art and general principles defined herein may be implemented in other embodiments without departing from the spirit or scope of the present disclosure. Hence, the present disclosure is not limited to the embodiments disclosed herein, but is to conform to the widest scope in accordance with principles and novel features disclosed herein.

The invention claimed is:

1. A fluorescence microscopic imaging method, comprising: after a to-be-detected sample plate is placed,
    lightening, according to an experimental requirement, at least one monochromatic fluorescence excitation light source with a same color among a plurality of monochromatic fluorescence excitation light sources as a target light source, wherein monochromatic fluorescence excitation light emitted by each of the plurality of monochromatic fluorescence excitation light sources obliquely enters a preset detection region of the to-be-detected sample plate;
    collecting, at a side of the to-be-detected sample plate facing away from the target light source, fluorescence of particles within the preset detection region excited by irradiation of monochromatic fluorescence excitation light emitted by the target light source, and magnifying the preset detection region a preset number of times;
    filtering the excited fluorescence of the particles within the preset detection region; and
    acquiring a fluorescence image of the preset detection region.

2. The fluorescence microscopic imaging method according to claim 1, wherein after the target light source is lightened and before the monochromatic fluorescence excitation light emitted by the target light source enters the to-be-detected sample plate, the method further comprises:
    converging the monochromatic fluorescence excitation light emitted by each monochromatic fluorescence excitation light source among the target light source.

3. A fluorescence microscopic imaging apparatus, comprising:
    a light source device comprising a plurality of monochromatic fluorescence excitation light sources and a control system electrically connected to the plurality of monochromatic fluorescence excitation light sources; wherein the plurality of monochromatic fluorescence excitation light sources are arranged around a central axis of an imaging light path composed of an objective lens and an image acquisition device, and monochromatic fluorescence excitation light emitted by each of the plurality of monochromatic fluorescence excitation light sources and the central axis of the imaging light path intersect at a preset position on a sample placing platform; and the control system lightens, according to an experimental requirement, at least one monochromatic fluorescence excitation light source with a same color among the plurality of monochromatic fluorescence excitation light sources as a target light source;
    the sample placing platform arranged at a position where monochromatic fluorescence excitation light emitted by the plurality of monochromatic fluorescence excitation light sources intersects and configured to place a to-be-detected sample plate, wherein a preset detection region of the to-be-detected sample plate is arranged at the preset position on the sample placing platform;
    the objective lens arranged at a side of the sample placing platform facing away from the light source device;
    an emitting light filtering module arranged at a side of the objective lens facing away from the sample placing platform; and
    the image acquisition device arranged at a side of the emitting light filtering module facing away from the objective lens.

4. The fluorescence microscopic imaging apparatus according to claim 3, wherein the light source device further comprises:
    a bright field light source, wherein full-band white light emitted by the bright field light source is toward the sample placing platform and coincides with the central axis of the imaging light path.

5. The fluorescence microscopic imaging apparatus according to claim 3, wherein the monochromatic fluorescence excitation light source is a monochromatic LED fluorescence excitation light source.

6. The fluorescence microscopic imaging apparatus according to claim 5, wherein the light source device further comprises:
    an excitation light filter arranged in an irradiation direction of the monochromatic LED fluorescence excitation light source and arranged between the monochromatic LED fluorescence excitation light source and the sample placing platform.

7. The fluorescence microscopic imaging apparatus according to claim 3, wherein the monochromatic fluorescence excitation light source comprises:
    a white light excitation light source; and
    an excitation light filter arranged in an irradiation direction of the white light excitation light source and arranged between the white light excitation light source and the sample placing platform.

8. The fluorescence microscopic imaging apparatus according to claim 3, wherein the emitting light filtering module is an emitting light filtering turntable, a plurality of emitting light filtering regions are provided at a periphery of the emitting light filtering turntable, and a pass band of each of the plurality of emitting light filtering regions is a band of fluorescence emitted by particles within the to-be-detected sample plate and excited by the monochromatic fluorescence excitation light source with a certain color.

9. The fluorescence microscopic imaging apparatus according to claim 3, wherein the light source device further comprises:
    a light converging module arranged in an irradiation direction of the monochromatic fluorescence excitation light source and arranged between the monochromatic fluorescence excitation light source and the sample placing platform.

10. The fluorescence microscopic imaging apparatus according to claim 9, wherein the light converging module is a light converging lens set comprising a plurality of lenses or a light converging lens.

11. The fluorescence microscopic imaging apparatus according to claim 3, wherein the image acquisition device is an eyepiece or a camera.

* * * * *